(12) United States Patent
Hughes et al.

(10) Patent No.: US 6,503,958 B2
(45) Date of Patent: Jan. 7, 2003

(54) BIOMATERIALS

(75) Inventors: Timothy Charles Hughes, Ferntree Gully (AU); Gordon Francis Meijs, Murrumbeena (AU); Hassan Chaouk, Atlanta, GA (US); John Gerard Steele, North Rocks (AU); Graham Johnson, Peakhurst (AU)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/929,396

(22) Filed: Aug. 14, 2001

(65) Prior Publication Data
US 2002/0103538 A1 Aug. 1, 2002

Related U.S. Application Data

(63) Continuation of application No. PCT/EP00/01267, filed on Feb. 16, 2000.

(30) Foreign Application Priority Data

Feb. 18, 1999 (DE) .......................................... 99103165

(51) Int. Cl.⁷ ................................................. C08J 9/28
(52) U.S. Cl. ......................................... 521/64; 521/145
(58) Field of Search .................................... 521/145, 64

(56) References Cited

U.S. PATENT DOCUMENTS

| 5,076,844 | A | * | 12/1991 | Fock et al. |
| 5,078,844 | A | | 1/1992 | Katsuma ..................... 205/149 |
| 5,783,299 | A | * | 7/1998 | Miyashita et al. |
| 6,224,774 | B1 | * | 5/2001 | DeSimone et al. |
| 6,290,853 | B1 | * | 9/2001 | Allmer et al. |

FOREIGN PATENT DOCUMENTS

EP 0373 384 B1 10/1992

* cited by examiner

Primary Examiner—Morton Foelak
(74) Attorney, Agent, or Firm—R. Scott Meece; Jian Zhou; Richard I. Gearhart

(57) ABSTRACT

The present invention relates to porous polymers incorporating dihydroperfluoroalkyl acrylates and methacrylates and the like and their production. The invention also relates to the use of polymers derived from dihydroperfluoroalkyl acrylates and methacrylates and like compounds, in both porous and non-porous forms, as substrates for the attachment and growth of mammalian cells and tissue. The invention also relates to the use of polymers derived from dihydroperfluoroalkyl acrylates and methacrylates as components of medical devices and prostheses, including implanted devices.

18 Claims, No Drawings

BIOMATERIALS

This is a continuation of International Application No. PCT/EP00/01267, filed Feb. 16, 2000, the contents of which are incorporated herein by reference.

The present invention relates to porous polymers incorporating dihydroperfluoroalkyl acrylates and methacrylates and the like and their production. The invention also relates to the use of polymers derived from dihydroperfluoroalkyl acrylates and methacrylates and like compounds, in both porous and non-porous forms, as substrates for the attachment and growth of mammalian cells and tissue. The invention also relates to the use of polymers derived from dihydroperfluoroalkyl acrylates and methacrylates as components of medical devices and prostheses, including implanted devices. In many applications it has been found advantageous for polymers to be porous. The degree of porosity required depends on the application. For example, membrane filtration depends on the use of microporous polymers to effect separations of various materials; macroporous sheets of chemically resistant polymers find extensive use as dividers in cells for electrolysis or electricity storage. Furthermore, porosity is often advantageous in synthetic polymers used in medical devices and prostheses implanted into tissue. This is the case where vascularisation of the implant is preferred or required, in which case the porosity enhances ingrowth of the blood vessels. It is also the case for some implants into non-vascular tissue, such as the case of a corneal onlay. U.S. Pat. No. 5,713,957 teaches that, in epikeratoprostheses, transmission of nutrients is an important factor for the maintenance of a healthy epithelium. Many other applications of polymers in medicine or surgery also require porosity or are optimal when the substrate is porous. These include artificial skins, drug delivery reservoirs, and soft tissue implants.

It is often useful for the porous polymer to be transparent and resistant to fouling and deposition. This is the case for some industrial membrane applications where the transparency allows inspection of the integrity of the membrane. Transparency of a synthetic polymer or porous polymer can also be an advantage for certain biomaterial applications, including for example the case of wound dressings where the transparency of the material allows for the progress of wound healing to be monitored without the dressing needing to be removed, or for some cases of implanted materials, an example being that of ocular implants.

Much of the prior art concerning cell and tissue colonisation of synthetic biomaterials teaches that adhesion of cells to hydrophobic polymeric substrates requires the surface chemistry of the synthetic polymer to be specifically modified to facilitate the adhesion and growth of cells. Stimulation of cellular attachment via adsorption or covalent attachment of one or more cell-adhesive molecules (such as fibronectin, vitronectin or collagen) or fragments thereof has also been used.

WO96/31548 discloses a class of materials based on perfluoroalkylpolyether macro-monomers, which in both their porous and non-porous forms can act as cell growth substrates and are suitable for use as biomaterials, particularly in ocular applications. WO96/31548 also discloses perfluoroalkylpolyether-containing compositions copolymerised with comonomers including minor amounts of dihydroperfluorooctyl acrylate. Although perfluoropolyethers as a general class of materials have many advantages, they suffer limitations in terms of cost and difficulty of purification. It would be useful if more readily available and simple monomers could be found with advantageous properties in terms of cell growth and/or being fabricated with porosity whilst maintaining clarity. We have now found that polymers and copolymers that are devoid of perfluoroalkylpolyether units but are based on free radically polymerisable monomers containing residues derived from fluorine containing alcohols and amines possess these properties and are particularly suitable as biomaterials, artificial cornea substrates and for use in other cell growth and membrane applications.

According to one aspect of the present invention there is provided a porous polymer that is obtained by polymerising a polymerisable component comprising (i) a free radically polymerisable unsaturated monomer of formula

$$Q-X-A \qquad (1),$$

wherein Q is a radical of formula

(2)

$Q_1$ is a radical of formula

(3a)

or

(3b)

(alk) is linear or branched $C_2$–$C_{12}$-alkylene, (alk') is linear or branched $C_1$–$C_{12}$-alkylene, R is an olefinically unsaturated copolymerisable radical having from 2 to 24 carbon atoms which may be further substituted, each of s and t is independently of the other the number 0 or 1, X is a group —O—, —S— or —NR$_1$— and R$_1$ is hydrogen, $C_1$–$C_4$-alkyl or a radical A, and A is a radical of formula

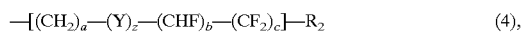
$$-[(CH_2)_a-(Y)_z-(CHF)_b-(CF_2)_c]-R_2 \qquad (4),$$

wherein $R_2$ is hydrogen or fluorine, Y is a group —N(R$_3$)SO$_2$—, —OSO$_2$—, —OC(O)— or —N(R$_3$)C(O)—, R$_3$ is hydrogen or $C_1$–$C_4$-alkyl, z is an integer of 0 or 1, a is an integer from 1 to 15, b is an integer from 0 to 6, and c is an integer from 1 to 20;

or A is partly or wholly fluorinated $C_4$–$C_8$-cycloalkyl, and optionally (ii) a comonomer and/or (iii) a crosslinker, wherein the porous polymer has a water content when fully swollen in water which is higher than that of the same polymer if polymerised under conventional conditions.

Suitable substituents on the olefinic $C_2$–$C_{24}$ radical R are, for example, $C_1$–$C_4$alkoxy, halogen, phenyl or carboxy. R is, for example, a radical of formula

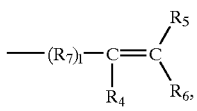
(5)

wherein l is the number 0 or 1, $R_4$ is hydrogen, $C_1$–$C_4$-alkyl or halogen, each of $R_5$ and $R_6$ independently of the other is hydrogen, $C_1$–$C_4$-alkyl, phenyl, carboxy or halogen, and $R_7$ is linear or branched $C_1$–$C_{12}$-alkylene or unsubstituted or $C_1$–$C_4$-alkyl- or $C_1$–$C_4$-alkoxy-substituted phenylene or $C_7$–$C_{12}$-aralkylene.

When $R_7$ is a phenylene radical, it is, for example, unsubstituted or methyl- or methoxy-substituted 1,2-, 1,3- or 1,4-phenylene. Preferably, $R_7$ as a phenylene radical is 1,3- or 1,4-phenylene.

When $R_7$ is an aralkylene radical, it is, for example, unsubstituted or methyl- or methoxy-substituted benzylene. Preferably, $R_7$ as an aralkylene radical is the 1,3- or 1,4-phenylenemethylene radical.

$R_7$ is preferably unsubstituted or methyl- or methoxy-substituted phenylene or phenylene-methylene or $C_1$–$C_{12}$alkylene, more preferably 1,3- or 1,4-phenylene or $C_1$–$C_6$alkylene, especially $C_1$–$C_2$alkylene and most preferably methylene.

l is the number 1 or, preferably, the number 0. $R_4$ is preferably hydrogen, methyl or chlorine and most preferably hydrogen or methyl.

Each of $R_5$ and $R_6$ independently of the other is preferably hydrogen, carboxy, chlorine, methyl or phenyl. In a preferred embodiment of the invention, $R_5$ is hydrogen, chlorine, methyl or phenyl and $R_6$ is hydrogen or carboxy. Most preferably, $R_5$ and $R_6$ are each hydrogen.

Examples of suitable radicals R are vinyl, 1-methylvinyl, 2-propenyl, allyl, 2-butenyl, o-, m- or p-vinylphenyl, styryl, 2-carboxyvinyl, 2-chloro-2-carboxyvinyl, 1,2-dichloro-2-carboxyvinyl, 1,2-dimethyl-2-carboxyvinyl and 2-methyl-2-carboxyvinyl.

Especially preferred radicals R correspond to formula (5) wherein l is 0, $R_4$ is hydrogen or methyl, $R_5$ is hydrogen, methyl, chlorine or phenyl, in particular hydrogen, and $R_6$ is carboxy or particularly hydrogen.

Other especially preferred radicals R correspond to the above formula (5) wherein l is 1, $R_7$ is 1,3- or 1,4-phenylene or $C_1$–$C_6$-alkylene, especially $C_1$–$C_2$-alkylene, $R_4$ is hydrogen or methyl and $R_5$ and $R_6$ are each hydrogen.

(alk) is preferably $C_2$–$C_6$-alkylene, more preferably $C_2$–$C_4$-alkylene and in particular ethylene. (alk') is preferably $C_1$–$C_4$-alkylene, especially methylene or 1,1-dimethylmethylene.

One group of suitable radicals Q corresponds to the above formula (2) wherein s is 0 and $Q_1$ is a radical of the above formula (3a) wherein t is 0 and for R the above given meanings and preferences apply. A second group of suitable radicals Q corresponds to the above formula (2) wherein s is 1 and $Q_1$ is a radical of the above formula (3a) wherein t is 0 and for R the above given meanings and preferences apply. Another group of suitable radicals Q corresponds to the above formula (2) wherein s is 1 and $Q_1$ is a radical of the above formula (3a) wherein t is 1 and for R and (alk) each the above given meanings and preferences apply. Still a further group of suitable radicals Q corresponds to the above formula (2) wherein s is 0 and $Q_1$ is a radical of the above formula (3b) wherein for R and (alk') each the above given meanings and preferences apply.

Especially preferred radicals —Q correspond to the formula

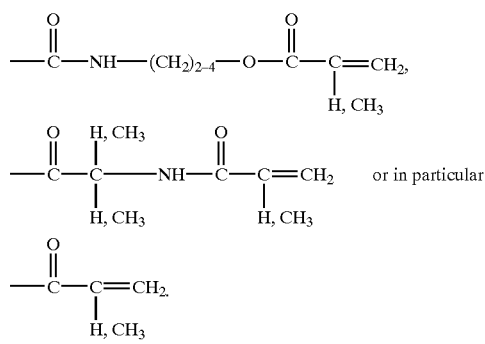

X is preferably a group —O— or —NR$_1$—, more preferably —O—, —NH—, —N($C_1$–$C_2$-alkyl)- —N—A, wherein the above and below given meanings and preferences for A apply, and is most preferably —O—, —NH— or —N($C_1$–$C_2$-alkyl) and in particular —O—.

Variable A as fluorinated cycloalkyl denotes preferably a 5- or preferably 6-membered cycloaliphatic ring which is partly or wholly fluorinated and is further unsubstituted or substituted by methyl or mono-, di- or trifluoromethyl. Variable A preferably denotes partly or wholly fluorinated cyclohexyl which is further unsubstituted. An example of a particularly preferred fluorinated cycloalkyl radical is perfluorocyclohexyl.

$R_2$ in formula (4) denotes preferably fluorine. $R_3$ is preferably $C_1$–$C_4$-alkyl and more preferably methyl or ethyl.

The meanings given above for Y are to be understood that the left bond is in general directed to a $CH_2$ group, and the right bond is directed to a CHF or $CF_2$ group. Y is preferably a group —N($R_3$)$SO_2$— wherein the above-given meanings and preferences apply for $R_3$. Variable z is preferably an integer of 0.

Variable a is preferably an integer from 1 to 4, more preferably 1 or 2 and in particular 1. Variable b is preferably an integer from 0 to 4 and in particular 0. Variable c is preferably an integer from 1 to 15, more preferably 1 to 10 and in particular 6 to 10.

Variable A is preferably a radical of the above-given formula (4) and in particular a radical of the formula $$-(CH_2)_a-(CF_2)_c-R_2 \qquad (4a),$$

wherein $R_2$ is hydrogen or fluorine, a is an integer of 1 or 2, and c is an integer from 1 to 20, preferably 1 to 15 and in particular 1 to 10. In a particular preferred embodiment of the invention A is a radical of formula (4a) above, wherein $R_2$ is fluorine, a is an integer of 1, and c is an integer of from 1 to 20, preferably 1 to 15, more preferably 1 to 10 and in particular 6 to 10.

Preferably the fluorine-containing moiety A contains a fluorine to hydrogen ratio of greater than 50%. More preferably A is highly fluorinated. That is to say that the fluorine to hydrogen ratio is greater than 70%.

Examples of particularly preferred compounds of formula (1) are dihydroperfluorooctyl acrylate and methacrylate, tetrahydroperfluorooctyl acrylate and methacrylate, dihydroperfluorohexyl acrylate and methacrylate, N-dihydroperfluorooctyl acrylamide and methacrylamide, N,N-bis(dihydroperfluorooctyl)acrylamide and methacrylamide, N-methyl-N-dihydroperfluorooctyl acrylamide. It is preferable that the length of the perfluorinated chain be 6 to 10 carbons long to obtain a material with a refractive index similar to tear film. However, this does not preclude the use of a combination of different length perfluorinated chains, ie less than 6 and greater than 10 to result in a material that has a refractive index similar to tear film or the use of perfluorinated chains greater than 10 carbons in order to counteract the high refractive indexes of other additives in the formulation. Also in some non-ocular applications matching refractive index of the material to tear film may not be important and hence the perfluorinated chain length may be outside the preferred range.

The polymerisable component underlying the polymers of the invention may contain one or more different monomers of formula (1), preferably one monomer of formula (1). The amount of monomer of formula (1) used in the polymerisable component is, for example, in the range of from 20 to 100%, preferably in the range of 45 to 100%, more preferably in the range of 60 to 100%, more preferably in the range of 80 to 99.9% and particularly preferably in the range of 90 to 99.5% in each case by weight of the entire polymerisable component.

In addition to a monomer of formula (1), further comonomers comprising one or more ethylenically unsaturated groups may be incorporated into the polymerisable component which can enter into a reaction to form the copolymers of the invention. It is preferred that the ethylenically unsaturated group be selected from the group consisting of acryloyl, methacryloyl, styryl, acrylamido, acrylamidoalkyl, or urethanemethacrylate, or any substituted derivatives thereof.

A comonomer present in the polymerisable component can be hydrophilic or hydrophobic or a mixture thereof. Suitable comonomers are, in particular, those which are usually used in the production of contact lenses and biomedical materials. A hydrophobic comonomer is taken to mean a monomer which typically gives a homopolymer which is insoluble in water and can absorb less than 10% by weight of water. Analogously, a hydrophilic comonomer is taken to mean a monomer which typically gives a homopolymer which is soluble in water or can absorb at least 10% by weight of water.

Suitable hydrophobic comonomers are, without limitation thereto, $C_1$–$C_{18}$-alkyl and $C_3$–$C_{18}$-cycloalkyl acrylates and methacrylates, $C_3$–$C_{18}$-alkylacrylamides and -methacrylamides, acrylonitrile, methacrylonitrile, vinyl $C_1$–$C_{18}$-alkanoates, $C_2$–$C_{18}$-alkenes, $C_2$–$C_{18}$-halo-alkenes, styrene, ($C_1$–$C_8$-alkyl)-styrenes, fluorinated styrenes, $C_1$–$C_8$-alkyl vinyl ethers, $C_3$–$C_{12}$-perfluoroalkylethylthiocarbonylaminoethyl acrylates and methacrylates, acryloxy- and methacryloxyalkylsiloxanes, N-vinylcarbazole, $C_1$–$C_{12}$-alkyl esters of maleic acid, fumaric acid, itaconic acid, mesaconic acid and the like.

Preference is given, for example, to acrylonitrile, $C_1$–$C_4$alkyl esters of vinylically unsaturated carboxylic acids having 3 to 5 carbon atoms or vinyl esters of carboxylic acids having up to 5 carbon atoms.

Examples of suitable hydrophobic comonomers are methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, butyl acrylate, vinyl acetate, vinyl propionate, vinyl butyrate, vinyl valerate, styrene, perfluorostyrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tristrimethylsilyloxysilylpropyl methacrylate (hereinafter: Tris methacrylate), tristrimethylsilyloxysilylpropyl acrylate (hereinafter: Tris acrylate), 3-methacryloxy propylpentamethyldisiloxane and bis (methacryloxypropyl)tetramethyldisiloxane.

Preferred examples of hydrophobic comonomers are methyl methacrylate, Tris acrylate, Tris methacrylate and acrylonitrile.

Suitable hydrophilic comonomers are, without this being an exhaustive list, hydroxyl- or amino-substituted $C_1$–$C_8$-alkyl acrylates and methacrylates, acrylamide, methacrylamide, ($C_1$–$C_8$-alkyl)acrylamides and -methacrylamides, ethoxylated acrylates and methacrylates, hydroxyl-, amino- or sulfo-substituted ($C_1$–$C_8$-alkyl) acrylamides and -methacrylamides, hydroxyl-substituted $C_1$–$C_8$-alkyl vinyl ethers, acrylic or methacrylic acid, N-vinylpyrrole, N-vinyl-2-pyrrolidone, 2-vinyloxazoline, 2-vinyl-4,4'-dialkyloxazolin-5-one, 2- and 4-vinylpyridine, allyl alcohol, zwitterionic monomers such as a N-alkylacrylamide or N-alkylmethacrylamide comprising a quaternized amino group and a sulfonic acid group in the alkyl moiety, and the like.

Examples of suitable hydrophilic comonomers are hydroxyethyl methacrylate (HEMA), hydroxyethyl acrylate, hydroxypropyl acrylate, acrylamide, methacrylamide, N,N-dimethylacrylamide (DMA), N,N-dimethylaminoethyl methacrylate (DMAEMA), trimethylammonium-2-hydroxypropylmethacrylate hydrochloride, 3-[(2-acrylamido-2-methyl-propyl)-dimethylamino]-propanesulfonate, 2-acrylamido-2-methylpropanesulfonic acid (AMPS), allyl alcohol, vinylpyridine, glycerol methacrylate, N-(1,1-dimethyl-3-oxobutyl)acrylamide, N-vinyl-2-pyrrolidone (NVP), and the like.

Preferred hydrophilic comonomers are 2-hydroxyethyl methacrylate, N,N-dimethylacrylamide, N,N-dimethylaminoethyl methacrylate 3-[(2-acrylamido-2-methyl-propyl)-dimethylamino]-propanesulfonate and N-vinyl-2-pyrrolidone.

The preferred range for addition of individual comonomers into the polymerisable component is from 0 to 60% by weight and most preferably 0 to 40% by weight of the entire polymerisable component. In one preferred embodiment of the polymers of the invention, the underlying polymerisable component is devoid of a comonomer. In another preferred embodiment of the polymers of the invention, the underlying polymerisable component comprises from 1 to 60% or in particular from 1 to 50% by weight of the entire polymerisable component of one or more different comonomers, where the above meanings and preferences apply.

Examples of typical crosslinkers which may be used for the preparation of the polymers of the invention are low molecular weight di- or polyvinylic crosslinking agents such as allyl (meth)acrylate, mono- di-, tri- or tetraethylene glycol diacrylate or dimethacrylate, mono-, di-, tri- or tetraethylene glycol diurethane acrylate or -methacrylate, a $C_2$–$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol A diacrylate or dimethacrylate, methylene bisacrylamide or -bismethacrylamide, ethylene bisacrylamide or ethylene bismethacrylamide, triallyl phthalate, diallyl phthalate, or fluorinated alkylene diacrylates or methacrylates, for example, of the formula $$H_2C=CR_8-C(O)O-H_2C-(CF_2)_{1-10}-CH_2-O(O)C-CR_8=CH_2 \tag{6},$$

wherein $R_8$ is hydrogen or methyl, such as 2,2,3,3,4,4-hexafluoropentanediol diacrylate or methacrylate or 2,2,3, 3,4,4,5,5-octafluorohexanediol diacrylate or methacrylate.

The crosslinker is advantageously a low-molecular weight crosslinker having a weight average molecular weight of <1000, preferably of ≦750 and more preferably of ≦500.

Preferred crosslinker components (iii) of the polymers of the invention are mono- di-, tri- or tetraethylene glycol diacrylate or dimethacrylate or fluorinated compounds of formula (6) above. The polymerisable component may contain one or more different crosslinkers, preferably one crosslinker.

If the polmerisable component contains a crosslinker, the amount used is, for example, in the range of from 0.05 to 20%, preferably in the range of 0.1 to 10%, and more preferably in the range of 0.5 to 5%, in each case by weight of the entire polymerisable component.

One preferred embodiment of the invention relates to a porous polymer that is obtained by polymerising a polymerisable component consisting solely of one or more different monomers of formula (1) above. Another preferred embodiment of the invention relates to a porous polymer which is obtained by polymerising a polymerisable component consisting of one or more different monomers of formula (1) and a crosslinker wherein the above-given meanings and preferences apply in each case. Still a further preferred embodiment of the invention relates to a porous polymer which is obtained by polymerising a polymerisable component consisting of one or more different monomers of formula (1) above, one or more different comonomers and a crosslinker wherein the above-given meanings and preferences apply in each case.

Non-porous polymers may be obtained from the polymerisable component of the invention in conventional manner, for example by (co)polymerising one or more monomers of formula (1) and optionally one or more comonomers, crosslinkers and/or further additives to afford a transparent polymer in the presence of a suitable initiator. Standard methods well known in the art for effecting polymerisation may be utilized, with free radical polymerisation being preferred. Free radical polymerisation can be simply carried out by radiating (using ultraviolet light) the polymerisable component containing a photoinitiator, such as benzoin methylether, in an appropriate container or vessel. The mixture is irradiated for a sufficient time to enable polymerisation between monomers to take place. Alternatively, redox initiation or thermal initiation using a thermal initiator such as azobisisobutyronitrile, can be employed.

The photochemical initiation of the monomer mixture using a photoinitiator such as Darocure 1173 (registered trademark of Ciba-Geigy AG) is the preferred polymerisation method.

The polymers of the invention are preferably produced in porous form. Porosity may be introduced by any known means in the art as disclosed for example in U.S. Pat. Nos. 5,244,799, 5,238,613 or 4,799,931 or in PCT applications WO 90/07575 or WO 91/07687.

One of the essential distinctive features of porous polymers made from a polymerisable component of the invention is that they have a water content when fully swollen in water which is higher than that of the same polymer if polymerised under conventional conditions. The water contents of the porous polymers of the invention, when fully swollen in water, is for example from 5 to 60% by weight, preferably from 10 to 60% by weight, even more preferably from 20 to 55% by weight and particularly preferably from 25 to 50% by weight. The above-given definition for porous polymers is to be understood in the context of this invention in that the claimed porous polymers do have their porosity, and the higher water content resulting therefrom, in the absence of any mechanical process steps following the polymerisation step, such as mechanical drilling or etching steps. "Conventional conditions" are to be understood that said conditions most preferably exclude any porosity promoting conditions, while porosity promoting conditions are chosen for making the porous polymers of the present invention.

Such porosity promoting conditions are essentially the use of porogens during polymerisation of the polymerisable component comprising monomer(s) of formula (1) and optionally further comonomer(s) and crosslinker(s) in the presence of initiator(s) or other additives. After polymerisation the porogens are removed by extraction or by chemical decomposition followed by extraction. Porogens can be made up from, but not limited by microemulsion systems, emulsion systems, large macromolecules such as a polyethylene glycol (PEG) or polypropylene glycol (PPG), dextrans, phase separations (solvents/non-solvents systems), gelling agents, self assembly structures, degradable networks, and bicontinuous microemulsion systems.

It will be appreciated, however, that highly fluorinated monomers possess unusual characteristics in their interaction with other substances. An unusually low surface energy is one such characteristic. Another characteristic is low solubility in many solvents, especially water. The low surface energy and low propensity to adsorb and dissolve many common materials is, in part, responsible for their outstanding resistance to fouling and degradation and the utility of fluoropolymers in non-stick and soiling resistant applications. A consequence of the low surface area and solubility of fluorochemicals is that stable emulsions and microemulsions in aqueous and other common media are difficult to achieve. For example, standard surfactants well known in the art are generally ineffective in stabilising aqueous microemulsions containing high proportions of fluoroacrylates.

According to another aspect of this invention, we have now found a process that is particularly suited to the production of the porous polymers described herein. The process comprises the steps of:

a) forming a mixture comprising a polymerisable component and an organic solvent, wherein the polymerisable component comprises compounds (i) and optionally (ii) or (iii) given above;

b) polymerising said mixture wherein immediately after the polymerisation of said mixture at least a substantial proportion of said organic solvent is in the form of a discrete phase and wherein said discrete organic solvent phase forms and interpenetrating network throughout the mixture or is dispersed throughout the mixture; and c) removing the discrete organic solvent phase.

Regarding the polymerisable component the above-given meanings and preferences apply.

The organic solvent is preferably selected from the group consisting of short chain alcohols, amines or ethers. The short chain alcohols, amines or ethers may be cyclic, branched or linear. Branched chain compounds are particularly preferred. The number of carbon atoms within the short chain compound may be from 1–12; it is preferred, however, that the number is from 2–8. Examples of preferred organic solvents are 1-propanol, isopropanol, diisopropyl ether, 2- or 3-hexanol, cyclopentanol, 3-hexylamine and isopropylamine. The use of a $C_2$–$C_8$-alcohol is particularly preferred.

The polymerisable component may be mixed with the organic solvent and other optional components by any convenient means. For example, the polymerisable component may be mixed with the organic solvent and other optional components by shaking or stirring. The order in which the components are added is not narrowly critical. The various components which make up the polymerisable component do not need to be combined prior to incorporation in the mixture. The mixture may be in the form of a homogeneous solution or may have the organic solvent as a distinct phase, such as in the form of a dispersion, microemulsion or preferably a co-continuous microemulsion. The form of the mixture prior to polymerisation is not narrowly critical since it is the form of the mixture during polymerisation which controls the morphology of the porous polymer.

Minor amounts of property modifying components may optionally be added to the mixture before polymerisation. For example, other solvents may be added to control pore size and morphology. Suitable solvents include ethyl acetate, dimethyl formamide, water and fluorinated alcohols.

Surfactants, preferably fluorinated surfactants may be incorporated into the mixture. The use of surfactants is an effective means of controlling the size and density of the pores. Non-ionic surfactants containing fluorine are preferred. Particularly preferred surfactants include commercially available fluorinated surfactants such as Zonyl (DuPont) and Fluorad (3M). Zonyl FS300 (DuPont) which is made up of a perfluorinated hydrophobic tail and hydrophilic poly(ethylene oxide) head group, is a particularly preferred surfactant for use in the process.

Polymerisable surfactants known to the art and zwitterionic compounds, such as 2-acryloyloxyethylphosphoryl choline, 10-methacryloyloxydecylphosphoryl choline and like compounds, are also preferred additives for control of wettability and morphology.

The mixture may be polymerised by any convenient method generally as described above with reference to the initiation of the polymerisable component. Suitable polymerisation conditions will be apparent to those skilled in the art. Temperatures may range from −100 to 350 C. and pressures may range from below atmospheric to above atmospheric. Oxygen-free conditions may be used.

Immediately after polymerisation it is essential that a substantial proportion of the organic solvent is in the form of a discrete phase. The discrete organic solvent phase may be in the form of an interpenetrating network throughout the polymerised component or may be dispersed as droplets throughout the polymerised component.

It will be understood that by a substantial proportion of the organic solvent is in the form of a discrete phase it is meant that there is sufficient organic solvent phase to form either an interpenetrating network of organic solvent phase or a dispersion of organic solvent phase. It will be understood by the person skilled in the art that depending on the polymerisation component and the organic solvent a proportion of organic solvent may be adsorbed or retained in the polymerisation component and eventually in the porous polymer. Typically more than 60% of the organic solvent is in the form of a discrete phase immediately after polymerisation. It is preferred that greater than 80% of the organic solvent is in the form of a discrete phase, more preferably greater than 95% of the organic solvent is in the form of a discrete phase.

It is particularly preferred that the organic solvent phase forms an interpenetrating network in the polymerisation component resulting in the porous polymer having a reticulated porous morphology. The reticulated porous morphology may be an open-cell, sponge-like structure consisting of interconnected polymer globular particles or may have an open-cell structure with an array of interconnected generally spherical pores.

In another preferred embodiment the porous polymer may be in the form of a closed-cell structure with discrete pores dispersed throughout the polymer.

The organic solvent may be removed from the porous polymer by any convenient means. Suitable means for removal of solvent include evaporation, exchange with other solvents such as isopropyl alcohol and subsequently water or the solvent may be simply washed out of the porous polymer with a suitable solvent such as water.

The process of the present invention is useful for generating materials of various pore sizes and morphologies. The upper limit of average pore size of individual pores is about 5 microns, with 100 nanometers being typical, while pores of around 10 nanometers in diameter may also be obtained. The pores may form an interpenetrating network. It is more useful to characterise these morphologies in terms of permeability to molecules of defined molecular weight. This is described in the examples.

The morphology and porosity of the porous polymer may be controlled by altering the ratio of the organic solvent to the monomer. At high ratios of organic solvent, an open sponge-like structure consisting of interconnected polymer globular particles is obtained. At lower ratios, a reticular network of pores is obtained. At even lower ratios a closed-cell morphology is obtained.

Particularly useful embodiments of the present method have the organic solvent phase in the form of a continuous interpenetrating network structure which may be readily extracted to leave a porous perfluorinated polymeric material having a reticular network of pores allowing ready passage of fluid and small diameter particles through the porous polymer. The size and density of the pores may be controlled by the ratio of the polymerisable component to organic solvent. Minor changes can be effected by the use of surfactants as here in above described. The addition of a minor proportion of water also increases porosity.

With suitable selection, the resultant copolymers are optically transparent, having a refractive index that provides a good match with aqueous media, tissue and cellular material. As a result the copolymers of the invention are ideal for use as an ophthalmic device or a ocular prostheses, such as a corneal onlay or implant.

A further embodiment of the invention relates to the use of the non-porous and porous polymers of the invention for the manufacture of mouldings, in particular biomedical mouldings. Suitable mouldings are, for example, biomedical devices, e.g. ophthalmic devices such as contact lenses, intraocular lenses or artificial cornea comprising a polymer of the invention. Mouldings from porous polymers of the invention are particularly preferred and represent a further embodiment of the invention.

The polymers produced according to the present invention may be formed into other useful articles using conventional moulding and processing techniques as are well known in the art. Given the visual transparency of the polymers of the present invention, they may find use in tissue culture apparatus, optical instruments, microscope slides and the like.

A further aspect of this invention is the use of the porous polymers of the invention in film or sheet form as a membrane or a filter. Such polymer films may be laminated with another support film to form a composite. Such applications may involve permeability to gases or liquids.

The porous polymers of the present invention may be suitable for use as a membrane having a variety of applications including industrial membranes, capacitors, home reverse osmosis, implanted glucose monitors, encapsulated biological implants e.g. pancreatic islets, drug delivery patches, membrane distillation using osmotic pressure, sustained release of active compounds, immobilised ligands for use in bioreactors or biosensors. Other applications include wound healing dressings, biotechnology and biomedical applications including vascular grafts, drug delivery patches, materials for the sustained release of active compounds and ultrafiltration in the food, dairy, juice, low alcohol beer industries.

As the polymers of the invention, whether porous or non-porous, are generally biocompatible towards cells and are of a chemistry that is chemically stable, these polymers can be enhanced for particular applications by applying to the surface of the polymers a surface coating. Such a surface coating can be a hydrophilic coating applied by a dip coating process or by RF gas plasma deposition method or the covalent attachment of particular chemical species or molecule; alternatively, such a coating can be a gel applied to the surface of a porous polymer. Such as a coating for the purpose of further enhancing the cell growth characteristics of the polymer can be the covalent attachment or adsorption of a molecule such as fibronectin, vitronectin, laminin, thrombospondin, or a peptide sequence fragment thereof, or the covalent attachment or adsorption of a gel comprising or containing these proteins.

The polymers of the invention, whether porous or non-porous, are particularly useful as materials for the attachment and growth of human or animal cells in vivo or in vitro, medical implants (such as implantable semipermeable membrane materials, tissue implants in cosmetic surgery, implants containing hormone secreting cells such as pancreatic islet cells, breast implants, artificial joints, and the like), in artificial organs, tissue culture apparatus (such as bottles, trays, dishes and the like), in biological reactors (such as those used in the production of valuable proteins and other components by cell culture), as material for the fabrication of medical devices or as coating for biomedical or biomaterial devices or applications, such as coatings on vascular grafts, catheters, artificial pancreas and the like, or as material for ophthalmic devices, such as contact lenses, intraocular lenses or artificial cornea, or ocular prostheses, such as corneal implants.

Ocular prostheses, such as corneal implants, may be made by copolymerisation of the polymerisable components in moulds and, optionally, the resultant copolymer may be fabricated or machined to the desired conformation. Ocular prostheses may be made by other methods which are well known per se to those skilled in the art. Porosity may be provided as described above.

Corneal implants may be placed by way of conventional surgery techniques beneath, within, or through corneal epithelial tissue, or within the corneal stroma or other tissue layers of the cornea. Such implants may change the optical properties of the cornea (such as to correct visual deficiencies) and/or change the appearance of the eye, such as pupil coloration. A corneal implant may comprise an optical axis region which on implantation covers the pupil and provides visual acuity, and a less transparent region which surrounds the periphery of the optical axis region. Alternatively the implant may have the same visual acuity across its dimensions.

It has been found that the flow of high molecular weight tissue fluid components such as proteins and glycoproteins (for example, growth factors, peptide and protein hormones, and proteins associated with the transport of essential metals) and the like across a corneal implant, that is, between epithelial cells and stromal cells and even the endothelial layer and beyond, is important for long term maintenance and viability of tissue anterior and posterior to a corneal implant. Accordingly the corneal implant is advantageously prepared with a porosity sufficient to allow passage therethrough of tissue fluid components having a molecular weight greater than about 10,000 daltons, thereby providing for a flux of tissue fluid components in addition to small molecular weight nutrients (such as glucose, fats and amino acids) and respiratory gases between cells anterior of the implant and cells posterior thereof.

Preferably a corneal implant has a porosity sufficient to admit proteins and other biological macromolecules of a molecular weight up to and greater than 10,000 daltons, such as from 10,000 to 1,000,000 daltons, but not sufficient to admit cells and thus tissue invasion into the optical axis region of the corneal onlay. Where porosity of the implant is provided by pores, the optical axis region comprises a plurality of pores, the number of which is not in any way limiting, but which is sufficient to provide flow of tissue components between the anterior and posterior regions of an implant. Preferably, the pores formed within the optical axis region do not cause refraction of visible light to an extent that would cause any problem with regard to vision correction. It is to be understood that the term pore does not put any geometric limitation on the nature of the pores which may be of regular or irregular morphology. It should be recognized that not all pores may be of the same diameter.

Outside of the optical axis region, the corneal implant may have the same porosity as the optical axis region. Alternatively, this region of the implant surrounding the periphery of the optical axis region, which may be referred to as the skirt, may allow the ingrowth of cells of the cornea thereby assisting in anchorage of the implant to the eye.

Porosity in the skirt may be an inherent feature of the material from which the skirt is formed. In this regard it is to be appreciated that the skirt may be formed of the same material as the optical axis region and may be integral therewith. In this situation, pores of differing diameter may be formed in the optical axis region and the skirt. Alternatively, the skirt may be formed of a different material from the optical axis region, which material is of a higher porosity than the optical axis region so as to allow this tissue ingrowth. Preferably the skirt may be comprised of an optically transparent polymer as is the optical axis region, but alternatively, the skirt may be comprised of an optically non-transparent material or may be made of a porous material that is not optically transparent.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

The present invention is further described in the following non-limiting examples. If not otherwise specified, all parts are by weight. Temperatures are in degrees Celsius. Molecular weights of monomers or polymers are number average molecular weights if not otherwise specified.

EXAMPLE 1

Synthesis of 1,1-dihydroperfluorooctyl Acrylate

A solution of freshly distilled acryloyl chloride (2.2 ml, 27.5 mmol) in trichlorotrifluoro-ethane (50 ml) is added dropwise to an ice-cooled solution of 1,1-dihydroperfluorooctan-1-ol (10.0 g, 25.0 mmol) and anhydrous triethylamine (4.2 ml, 30.0 mmol) in trichlorotrifluoroethane (100 ml). The mixture is stirred at 0° C. under an argon atmosphere for 3 h. The mixture is filtered and the residue is extracted with trichlorotrifluoroethane (3×30 ml).

The combined filtrate is washed with an aqueous saturated solution of sodium hydrogen carbonate (50 ml) and with an aqueous saturated solution of sodium chloride (50 ml), and then dried over magnesium sulphate. The mixture is filtered and hydroquinone (200 mg) is added before the solvents are removed under reduced pressure at room temperature. Distillation at reduced pressure (b.p. 50° C./0.6 mmHg) give 1,1-dihydroperfluorooctyl acrylate (7.86 g, 70% yield, >92% purity) as a colourless oil. $^1$H n.m.r. (CDCl$_3$) d 4.66, br t, J 13.5 Hz, OCH$_2$; 5.92–6.26, m, 2H, and 6.46–6.60, m, 1H, CH$_2$=C.

EXAMPLES 2 TO 11

A mixture of 1,1-dihyroperfluorooctyl acrylate (50 parts), the solvent in Table 1 (50 parts) and ethylene glycol dimethacrylate (2.5 parts) is irradiated in a polypropylene flat mould in the presence of the free radical initiator, Darocure (1.5 parts) for 3 h.

Standard Procedure for Extraction

After demoulding, the resulting flat discs are extracted at room temperature in perfluorinated solvent (for example PF5060, Minnesota Mining and Manufacturing Company (3M) or Vertrel XF, Du Pont) for 24 hours, then placed in isopropyl acetate (IPAc) for 24 hours, then in isopropyl alcohol (IPA) for 24 hours, then into ethanol for 24 hours, then into 75:25 ethanol/water for 24 hours, then into 50:50 ethanol/water for 24 hours, then into 25:75 ethanol/water for 24 hours, then into water for 24 hours, and then into fresh water for a further three hours.

Procedure for Determining Porosity of Polymers Towards Bovine Serum Albumin

A flat 20 mm diameter polymer disk ("hydrated" by exchange with water as described above) is clamped between two chambers, one containing an 8 mg/ml solution of bovine serum albumin (BSA) in phosphate buffered saline (PBS) while the other chamber is filled with only PBS. After 24 h, a sample is removed from the PBS chamber and the U.V. absorbance is measured at 280 nm (A280) to determine whether any BSA has diffused through the centrally fixed membrane. A higher absorbance reading points to a higher rate of BSA diffusion and is therefore indicative of a structure with a relatively large pore size and/or a larger pore density. The results are shown in Table 1:

TABLE 1

Albumin transmissibility of materials from Examples 2 to 11 comprising dihydroperfluorooctyl acrylate monomers.

| Example # | Solvent used to introduce porosity | Absorbance of transmitted Bovine Serum Albumin after 24 h |
|---|---|---|
| 2 | methanol | 0.30 |
| 3 | ethanol | 0.83 |
| 4 | 1-propanol | 1.32 |
| 5 | 2-propanol | 0.34 |
| 6 | 2-hexanol | 1.08 |
| 7 | 2-butoxyethanol | 0.41 |
| 8 | 3-methyl-2-butanol | 0.68 |
| 9 | 3-methoxy-2-butanol | 0.42 |
| 10 | 3-pentanol | 0.66 |
| 11 | 4-methyl-2-pentanol | 0.41 |

The data indicates that the polymers of Examples 2 to 11 are each effectively porous towards molecules of molecular size up to that of bovine serum albumin, which is a globular protein of molecular weight 67,000 daltons.

EXAMPLES 12–30

The compositions as outlined in table 2 below are placed in each case in a polypropylene flat mould (0.2 mm thick) and polymerised for 3 hours under irradiation from 365 nm UV lamps. The abbreviations in the Table have the following meaning: Darocur=Darocur® 1173 (photoinitiator Ciba-Geigy); DHPFOA=dihydroperfluorooctyl acrylate; DHPFEA=dihydroperfluoroethyl acrylate; DHPFBA=dihydroheptafluorobutyl acrylate; THPFOA=tetrahydroperfluorooctyl acrylate; EGDMA=ethyleneglycol dimethacrylate; EGDA=ethyleneglycol diacrylate; TEGDMA=tetraethyleneglycol dimethacrylate; TEGDA=tetraethyleneglycol diacrylate; HEMA=2-hydroxyethyl methacrylate; DMA=N,N-dimethylacrylamide; DMAEMA=N,N-dimethylaminoethyl methacrylate; AMPPS=3-[(2-acrylamido-2-methyl-propyl)dimethylamino]-propanesulfonate; Propanol=n-propanol; IPAc=isopropyl acetate; Zonyl FSN=Zonyl FSN 100 (non-ionic fluorinated surfactant [DuPont]); Zonyl FSN=Zonyl FSO 100 (non-ionic fluorinated surfactant [DuPont]).

TABLE 2

(all data given in parts by weight):

| Example | 12 | 13 | 14 | 15 | 16 | 17 | 18 | 19 | 20 | 21 |
|---|---|---|---|---|---|---|---|---|---|---|
| Darocur | 3 | 1 | 1 | 1 | 0.25 | 0.5 | 0.16 | 1 | 0.2 | 1 |
| DHPFOA | 100 | 100 | 50 | 100 | 50 | 50 | 50 | 100 | 20 | |
| DHPFEA | | | | | | | | | | 101 |
| EGDMA | 5 | | 2 | 5 | 1 | 1 | 1 | | | |
| EGDA | | 5 | | | | | | 20 | | 6 |
| TEGDMA | | | | | | | | | 1 | |
| HEMA | 34 | | | 30 | | | | | | |
| DMA | | | 50 | 30 | | | | | | |
| DMAEMA | | | | | | | 5 | | | |
| AMPPS | | | | | 0.5 | | | | | |
| Propanol | 100 | 30 | 50 | 82 | 10 | 10 | 25 | 40 | 6 | 60 |
| Water | | | | | 5 | 10 | | | | |
| Zonyl FSN | | | | | 10 | 10 | | | | |
| Zonyl FSO | | | | | | 10 | | | | |

| Example | 22 | 23 | 24 | 25 | 26 | 27 | 28 | 29 | 30 |
|---|---|---|---|---|---|---|---|---|---|
| Darocur | 1 | 1 | 1 | 1 | 1 | 1 | 1 | 1 | 1 |

TABLE 2-continued (all data given in parts by weight):

| | | | | | | | | | |
|---|---|---|---|---|---|---|---|---|---|
| DHPFOA | | 34 | 250 | 250 | 330 | | | | 125 |
| THPFOA | | | | | | | | 50 | |
| DHPFBA | 44 | | | | | 96 | 95 | | |
| EGDMA | | 1 | 13 | 13 | 17 | | | | |
| EGDA | 2 | | | | | 5 | | 3 | |
| TEGDMA | | | | | | | | | 7.5 |
| TEGDA | | | | | | | 5 | | |
| HEMA | | 3 | | | | | | | |
| DMAEMA | | 3 | | | | | | | |
| Propanol | 26 | 40 | | 250 | | 57 | 57 | 30 | 75 |
| IPAc | | | 38 | | 65 | | | | |

The materials are extracted in each case following the standard procedure outlined in Examples 2 to 11. The materials are optically clear.

Standard Procedure for Porosity Measurement

A flat disc of the polymer of known thickness (normally 0.1 or 0.2 mm thickness) is clamped between two chambers. One chamber is filled with PBS buffer solution and the other with a protein solution (8 mg/ml) typically either bovine serum albumin, lysozyme, or tryptophane. The samples are left sitting for either 6 h or 24 h. Then the solution within the chamber that originally contained the buffer solution is removed and its UV spectrum measured. The absorption at 280 nm is recorded. The proteins have a maximum absorbance at 280 nm and so the observed absorbance at 280 nm is proportional to the amount of protein that has permeated through the membrane.

Protein Permeation Measurement (24 Hours)

| | Absorbance at 280 nm | | |
|---|---|---|---|
| Example | Bovine Serum Albumin | Lysozyme | Tryptophan |
| 12 | 0.06 | 0.5 | n.m. |
| 13 | 0.24 | 0.62 | 3.28 |
| 14 | 0.06, 0.02 | n.m. | n.m. |
| 15 | 0.07 | 1.246 | n.m. |
| 16 | 0.01 | 1.61 | 2.83 |
| 17 | 0.14 | 1.13 | 3.13 |
| 19 | 0.5 | 1.74 | 3.27 |
| 20 | 0.432 | >3.8 | >3.8 |
| 21 | 0.696 | 1.44 | >3.7 |
| 22 | 0.57 | 0.93 | >3.7 |
| 23 | 0.72, 0.65 | n.m. | n.m. |
| 25 | 0.65 | n.m. | n.m. |
| 27 | 0.075 | 0.016 | 0.027 |
| 28 | 0.02 | 0.02 | 0.02 |

The data indicate that all polymers except those of Examples 14, 27 and 28 are porous towards molecules of molecular size up to that of bovine serum albumin, which is a globular protein of molecular weight 67,000 daltons. The polymers of example 27 and 28 are not effectively porous towards either bovine serum albumin, lysozyme or tryptophan.

Standard Procedure for Cell Attachment and Growth Assay

Cultured bovine corneal epithelial cells (BCEp) between passage numbers 2 to 4 are used to determine the relative cell attachment and growth performance of each copolymer. Test polymers are cut into 6 mm diameter disks using a sterile biopsy punch with each sample prepared in triplicate. Replicates are transferred to individual wells of a 96-well format tissue culture polystyrene (TCPS) tray and left overnight at room temeperature in a phosphate buffered saline solution containing 120 µg/ml penicillin and 200 µg/ml streptomycin. Cells are seeded onto each sample surface, including replicates on TCPS alone, at a density of $5 \times 10^3$ cells/well and cultured for seven days in a culture medium containing Dulbecco's Minimal Essential Medium/Ham's F12 (50:50 v/v) supplemented with foetal bovine serum (FBS at concentration of 20% (v/v)), 60 µg/ml penicillin and 100 µg/ml streptomycin and maintained at 37° C. in a humidified atmosphere of 5% $CO_2$ in air. The culture medium is changed every second day. To determine the relative cell numbers present at day seven on each sample, the cells are incubated for 4 hours in a 0.5 mg/ml solution of MTT (a water soluble tetrazolium salt that is converted to a coloured, insoluble purple dye by dehydrogenase enzymes in living cells). The coloured end-product is solubilized with DMSO and absorbance values are measured on a plate reader (595 nm wavelength) and expressed as a percentage (±s.d.) of the absorbance value obtained for cells grown on a standard positive control surface, which iss commercially-sourced polystrene which has been treated for use in tissue culture (TCPS).

Standard Procedure for Corneal Tissue Outgrowth Assay

Replicates, 20 mm diameter, of each polymeric sample are transferred to individual wells of a 6-well tissue culture polystyrene (TCPS) tray and left overnight at room temperature in a phosphate buffered saline solution containing 120 µg/ml penicillin and 200 µg/ml streptomycin. Each formulation assays in triplicate. Corneas are excised from freshly enucleated cow's eyes and the endothelium is carefully removed using jewellers forceps. Most of the stroma is then removed leaving an intact epithelial layer with approximately 10% of the stroma still attached. Tissue explant disks, of 6 mm in diameter, are cut from the remaining epithelial layer with a sterile biopsy punch and each one placed epithelial side up onto the center of each replicate polymer disk. The explants are cultured in the absence of serum in a culture medium consisting of Dulbecco's Minimal Essential Medium/Ham's F12 supplemented with 5 ug/ml insulin, 5 µg/ml transferrin, 5 ng/ml selenious acid, 60 ug/ml penicillin and 100 ug/ml streptomycin. Explants are cultured for a period of eight days at 37° C. in a humidified atmosphere of 5% $CO_2$ in air and the culture medium is changed at day three and day six. On day eight, the explants are stained with methylene blue (1% w/v in borate buffer pH 8.4) and outgrowth areas measured by image analysis (Quantimet 570, Leica Cambridge). A mean (±s.d.) tissue outgrowth index (MI) is calculated by dividing the final spread area of each explant by it's initial tissue area. A tissue outgrowth index (MI) of 1.00 denotes zero outgrowth and indicates that the material surface does not support tissue outgrowth.

| Support | % BCEp Cell (sd) Attachment and growth | Migration Index (sd) |
|---|---|---|
| Tissue culture polystyrene | 100.00 (5.58) | 4.33 (0.56) |
| Example 20 material | 54.37 (7.163) | 2.62 (0.82) |

The data indicate that the polymer supports the attachment and growth of mammalian cells. The polymer also supports the outgrowth of epithelial tissue over the surface of the polymer. Both of these results also indicate that the polymer is generally biocompatible towards cells and tissue.

| Support | % BCEp Cell (sd) Attachment and Growth | Migration Index (sd) |
|---|---|---|
| Tissue culture polystyrene | 100.00 (6.00) | 5.35 (0.89) |
| Example 24 material | 98.65 (9.41) | 2.90 (0.14) |

The data indicate that the polymer supports the attachment and growth of mammalian cells. The polymer also supports the outgrowth of epithelial tissue over the surface of the polymer. Both of these results also indicate that the polymer is generally biocompatible towards cells and tissue.

| Support | % BCEp Cell (sd) Attachment and growth | Migration Index (sd) |
|---|---|---|
| Tissue culture polystyrene | 100.00 (4.75.) | 4.89 (0.40) |
| Example 25 material | 108.90 (5.53) | 1.00 (0.01) |

The data indicate that the polymer of Example 25 supports the attachment and growth of mammalian cells, to an equivalent extent to that of the positive control material (TCPS).

| Support | Migration Index (sd) |
|---|---|
| Tissue culture polystyrene | 5.35 (0.89) |
| Example 26 material | 3.23 (0.43) |

The data indicate that the polymer of Example 26 supports the outgrowth of epithelial tissue over the surface of the polymer. Both of these results also indicate that the polymer is generally biocompatible towards cells and tissue.

| Support | % BCEp Cell (sd) Attachment and growth | Migration Index (sd) |
|---|---|---|
| Tissue culture polystyrene (TCPS) | 100.00 (5.58) | 4.27 (0.33) |
| Example 27 material | 93.8 (13.01) | 2.33 (0.06) |

The data indicate that the polymer supports the attachment and growth of mammalian cells. The polymer also supports the outgrowth of epithelial tissue over the surface of the polymer. Both of these results also indicate that the polymer is generally biocompatible towards cells and tissue.

| Support | Migration Index (sd) |
|---|---|
| Tissue culture polystyrene (TCPS) | 4.27 (0.33) |
| Example 28 material | 2.89 (0.26) |

| Support | % BCEp Cell (sd) Attachment and growth | Migration Index (sd) |
|---|---|---|
| Tissue culture polystyrene (TCPS) | 100.00 (5.58) | 4.27 (0.33) |
| Example 29 material | 95.00 (4.00) | 2.03 (0.43) |

| Support | Migration Index (sd) |
|---|---|
| Tissue culture polystyrene (TCPS) | 8.83 (1.52) |
| Example 30 material | 3.11 (0.25) |

The data indicate that the polymers of Examples 28–30 all support the outgrowth of epithelial tissue over the surface of the polymer.

EXAMPLE 31

Measurement of Water Content (EWC)

1,3-Propane sultone (2.0 g) is added to three dried samples of the material prepared in Example 5 swelled in a 50:50 solution of Vertrel XF/methanol (10 ml). The mixture is heated under reflux overnight. The modified samples are then extracted following the standard procedure outlined in Examples 2–11. The equilibrium water content (EWC) of the 3 samples is measured and found to be 32.1%±0.6%.

In addition, the EWC of 8 samples of polymer according to Example 18 is measured and found to be 16.6%±1.7%.

What is claimed is:

1. A porous polymer that is obtained by polymerising a polymerisable component comprising (i) a free radically polymerisable unsaturated monomers of formula

 (1), wherein Q is a radical of formula

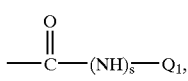
(2)

$Q_1$ is a radical of formula

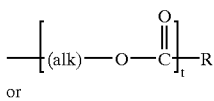
(3a)

or

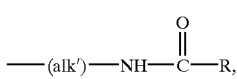
(3b)

(alk) is linear or branched $C_2$–$C_{12}$-alkylene, (alk') is linear or branched $C_1$–$C_{12}$-alkylene, R is an olefinically unsaturated copolymerisable radical having from 2 to 24 carbon atoms which may be further substituted, each of s and t is independently of the other the number 0 or 1, X is a group —O—, —S— or —NR$_1$— and R$_1$ is hydrogen, $C_1$–$C_4$-alkyl or a radical A, and A is a radical of formula

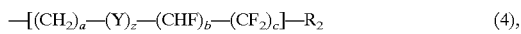
(4), wherein $R_2$ is hydrogen or fluorine, Y is a group —N(R$_3$)SO$_2$—, —OSO$_2$—, —OC(O)— or —N(R$_3$)C(O)—, R$_3$ is hydrogen or $C_1$–$C_4$-alkyl, z is an integer of 0 or 1, a is an integer from 1 to 15, b is an integer from 0 to 6, and c is an integer from 1 to 20;

or A is partly or wholly fluorinated $C_4$–$C_8$-cycloalkyl, and optionally (ii) a comonomer and/or (iii) a crosslinker, wherein the porous polymer has a water content when fully swollen in water which is higher than that of the same polymer if polymerised under conventional conditions.

2. A porous polymer according to claim 1, wherein Q corresponds to formula (2) wherein s is 0, $Q_1$ is a radical of the above formula (3a), t is 0 and R is a radical of formula

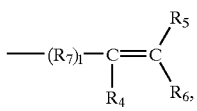
(5)

wherein l is the number 0, $R_4$ is hydrogen, $C_1$–$C_4$-alkyl or halogen, and each of $R_5$ and $R_6$ independently of the other is hydrogen, $C_1$–$C_4$-alkyl, phenyl, carboxy or halogen.

3. A porous polymer according to claim 1 or 2, wherein Q is a radical of formula

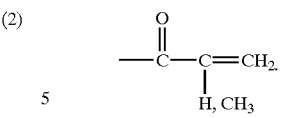

4. A porous polymer according to any one of claims 1 to 3, wherein X is —O—, —NH— or —N($C_1$–$C_2$-alkyl).

5. A porous polymer according to any one of claims 1 to 4, wherein A is a radical of formula (4), wherein $R_2$ is hydrogen or fluorine, z is 0, a is from 1 to 4, b is from 0 to 4, and c is from 1 to 10.

6. A porous polymer according to any one of claims 1 to 5, wherein A is a radical of formula

(4a), $R_2$ is hydrogen or fluorine, a is an integer of 1 or 2, and c is an integer from 1 to 10.

7. A porous polymer according to claim 1 wherein the polymerisable component comprises a monomer of formula (1), wherein Q is a radical of formula

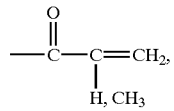

X is is —O—, —NH— or —N($C_1$–$C_2$-alkyl), and

A is a radical of formula

(4a), wherein $R_2$ is hydrogen or fluorine, a is an integer of 1 or 2, and c is an integer from 1 to 10.

8. A porous polymer according to any one of claims 1 to 7, wherein the polymerisable component consists of one or more different monomers of formula (1).

9. A porous polymer according to any one of claims 1 to 7, wherein the polymerisable component consists of one or more different monomers of formula (1) and a crosslinker.

10. A porous polymer according to claim 9, wherein the crosslinker is mono- di-, tri- or tetraethylene glycol diacrylate or dimethacrylate or a fluorinated compound of formula

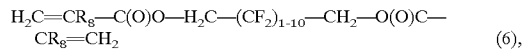
(6), wherein $R_8$ is hydrogen or methyl.

11. A porous polymer according to any one of claims 1 to 7, wherein the polymerisable component consists of one or more different monomers of formula (1), one or more different hydrophilic comonomers and a crosslinker.

12. A process for the production of a porous polymer according to claim 1, comprising the steps of:

a) forming a mixture comprising a polymerisable component and an organic solvent wherein the polymerisable component comprises a free radically polymerisable unsaturated monomer of formula (1) according to claim 1 and optional a further comonomer and/or crosslinker;

b) polymerising said mixture wherein immediately after the polymerisation of said mixture at least a substantial proportion of said organic solvent is in the form of a discrete phase and wherein said discrete organic solvent phase forms and interpenetrating network throughout the mixture or is dispersed throughout the mixture; and c) removing the discrete organic solvent phase.

13. A process according to claim 12, wherein the organic solvent is a $C_2$–$C_8$-alcohol.

14. A moulding comprising a porous polymer according to any one of claims 1 to 11.

15. A moulding according to claim 14, which is a biomedical device, in particular an ophthalmic device.

16. A moulding according to claim 14, which is a medical implant.

17. A moulding according to claim 14, which is an ocular prostheses, in particular a corneal implant.

18. A moulding according to claim 14, which is a wound healing dressing.

* * * * *